(12) United States Patent
Lietzau et al.

(10) Patent No.: US 11,236,063 B2
(45) Date of Patent: Feb. 1, 2022

(54) DIBENZOFURAN DERIVATIVES AND DIBENZOTHIOPHENE DERIVATIVES

(71) Applicant: MERCK PATENT GMBH, Darmstadt (DE)

(72) Inventors: Lars Lietzau, Rossdorf (DE); Achim Goetz, Alsbach-Haehnlein (DE); Harald Hirschmann, Darmstadt (DE); Martin Engel, Darmstadt (DE)

(73) Assignee: MERCK PATENT GMBH, Darmstadt (DE)

( * ) Notice: Subject to any disclaimer, the term of this patent is extended or adjusted under 35 U.S.C. 154(b) by 38 days.

(21) Appl. No.: 16/622,621

(22) PCT Filed: Jun. 11, 2018

(86) PCT No.: PCT/EP2018/065277
§ 371 (c)(1),
(2) Date: Dec. 13, 2019

(87) PCT Pub. No.: WO2018/228968
PCT Pub. Date: Dec. 20, 2018

(65) Prior Publication Data
US 2021/0139451 A1    May 13, 2021

(30) Foreign Application Priority Data
Jun. 14, 2017  (DE) ............ 10 2017 005 644.7

(51) Int. Cl.
*C07D 333/76* (2006.01)
*C07D 307/91* (2006.01)
*C09K 19/32* (2006.01)
*C09K 19/34* (2006.01)

(52) U.S. Cl.
CPC ......... *C07D 333/76* (2013.01); *C07D 307/91* (2013.01); *C09K 19/32* (2013.01); *C09K 19/3405* (2013.01); *C09K 19/3491* (2013.01); *C09K 2019/3408* (2013.01)

(58) Field of Classification Search
CPC ........ C09K 19/3491; C09K 2019/3408; C09K 19/32; C09K 19/3405; C07D 333/76; C07D 307/91
See application file for complete search history.

(56) References Cited

U.S. PATENT DOCUMENTS

| | | | |
|---|---|---|---|
| 7,018,685 B2 | 3/2006 | Schmidt et al. | |
| 8,444,877 B2 | 5/2013 | Chen et al. | |
| 9,512,102 B2 | 12/2016 | Reiffenrath et al. | |
| 2018/0030020 A1 | 2/2018 | Reiffenrath et al. | |
| 2018/0112132 A1* | 4/2018 | Li | C09K 19/322 |
| 2018/0208845 A1* | 7/2018 | Wang | C09K 19/0403 |
| 2018/0320071 A1* | 11/2018 | Meng | C09K 19/586 |
| 2019/0161679 A1* | 5/2019 | Hirschmann | C09K 19/3003 |
| 2020/0032143 A1* | 1/2020 | Takata | G02F 1/13 |

FOREIGN PATENT DOCUMENTS

| | | |
|---|---|---|
| DE | 102015002298 A1 | 9/2015 |
| DE | 102015004271 A1 | 10/2015 |
| EP | 2937342 B1 | 11/2016 |
| WO | 02055463 A1 | 7/2002 |
| WO | 09091884 A1 | 7/2009 |

OTHER PUBLICATIONS

International Search Report PCT/EP2018/065277 dated Jul. 17, 2019 (pp. 1-2).

* cited by examiner

*Primary Examiner* — Chanceity N Robinson
*Assistant Examiner* — Anna Malloy
(74) *Attorney, Agent, or Firm* — Millen White Zelano and Branigan, PC; John Sopp

(57) ABSTRACT

Compounds of the formula I

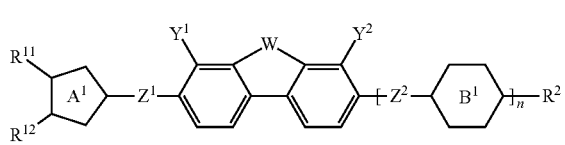

in which groups and parameters that occur have the definitions given in the disclosure. Preparation methods for these compounds. Uses of the compounds as components in liquid-crystalline media. Electrooptical display elements comprising the liquid-crystalline media.

11 Claims, No Drawings

DIBENZOFURAN DERIVATIVES AND DIBENZOTHIOPHENE DERIVATIVES

The invention relates to dibenzofuran and dibenzothiophene derivatives, to the use thereof in liquid-crystal mixtures, especially in liquid-crystal mixtures with negative dielectric anisotropy, and to the use of these liquid-crystal mixtures in liquid-crystal displays of the VA, PS-VA, IPS, PS-IPS or FFS type.

Liquid crystals have found a wide field of use since the first commercially employable liquid-crystalline compounds were found about 30 years ago. Known fields of use for conventional mixtures are especially displays for watches and pocket calculators, and also large display panels as used in railway stations, airports and sports arenas. Further fields of application are displays of portable and stationary computers, navigation systems and video applications. Particularly for the latter applications, high demands are made on switching times and the contrast of the images.

The effect of the spatial order of the molecules in a liquid crystal is that many of its properties are direction-dependent. Properties of significance for use in liquid-crystal displays are especially the anisotropies in the optical, dielectric and elastomechanical characteristics. According to whether the molecules are oriented with their longitudinal axes perpendicular or parallel to the two plates of a capacitor, the latter has a different capacitance; in other words, the dielectric constant ε of the liquid-crystalline medium is of different size for the two orientations. Substances having a greater dielectric constant in the case of perpendicular orientation of the longitudinal molecular axes to the capacitor plates than in the case of parallel arrangement are referred to as dielectrically positive. In other words: if the dielectric constant $\varepsilon_\parallel$ parallel to the longitudinal molecular axes is greater than the dielectric constant $\varepsilon_\perp$ perpendicular to the longitudinal molecular axes, the dielectric anisotropy $\Delta\varepsilon = \varepsilon_\parallel - \varepsilon_\perp$ is greater than zero. Most liquid crystals that find use in conventional displays are part of this group.

Important factors for dielectric anisotropy are both the polarizability of the molecule and permanent dipole moments. For application of a voltage to the display, the longitudinal axis of the molecules is aligned such that the greater of the dielectric constants becomes active. The strength of the interaction with the electrical field depends on the difference between the two constants.

In the case of the liquid-crystal molecules used in conventional liquid-crystal displays, the dipole moment oriented along the longitudinal molecular axis is greater than the dipole moment oriented perpendicular to the longitudinal molecular axis.

Liquid crystals in which the greater dipole moment is oriented parallel to the longitudinal axis of the molecule have already been used to develop very high-performance displays. This is usually done using mixtures of 5 to 20 components in order to aim for a sufficiently broad temperature range of the mesophase and short switching times and low threshold voltages. However, difficulties are still presented by significant viewing angle dependence in the case of liquid-crystal displays as used for laptops for example. The best image quality can be achieved when the surface of the display is perpendicular to the viewing angle of the viewer. If the display is tilted relative to the viewing direction, there is a deterioration in the image quality, a severe deterioration in some cases. For higher comfort, efforts are being made to make the angle by which the display can be tilted from the viewing angle of a viewer without any significant reduction in the image quality as large as possible. Recently, attempts have been made to improve the viewing angle dependence by using liquid-crystalline compounds having a greater dipole moment perpendicular to the longitudinal molecular axis than parallel to the longitudinal axis of the molecule. The dielectric anisotropy $\Delta\varepsilon$ in this case is negative. In the field-free state, these molecules are oriented with their longitudinal axis perpendicular to the glass surface of the display. As a result of application of an electrical field, they become oriented more or less parallel to the glass surfaces. In this way, it was possible to achieve an improvement in the viewing angle dependence. Displays of this kind are referred to as VA-TFT displays ("vertically aligned").

Further LC display modes that are being employed not only in TV applications but particularly also for small and medium-sized LC displays for use in portable devices, for example tablet PCs or smartphones, are the IPS and FFS (fringe field switching) mode, in which LC media with both negative and positive dielectric anisotropy are used.

FFS displays based on LC media with negative dielectric anisotropy have been described in S. H. Lee et al., Appl. Phys. Lett. 73(20), 1998, 2882-2883 and S. H. Lee et al., Liquid Crystals 39(9), 2012, 1141-1148.

Development in the field of liquid-crystalline materials is by no means complete as yet. To improve the properties of liquid-crystalline display elements, efforts are constantly being made to develop novel compounds that enable optimization of such displays.

The prior art discloses VA materials derived from dibenzofuran or from dibenzothiophene.

WO 02/055463 discloses compounds of the formula

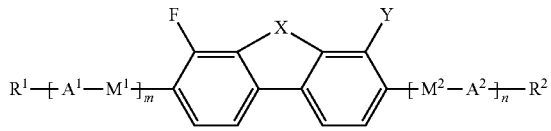

in which X may be O or S inter alia, Y may be F, $R^1$ and $R^2$ may be alkyl or alkoxy and the other parameters have the definitions specified therein. The compounds described therein have negative dielectric anisotropy, but have been developed for ferroelectric LC mixtures, and no values for the dielectric anisotropies of the individual substances are described. WO 2009/091884 discloses, in principle, compounds containing a five-membered carbocycle, including the compound of the following formula:

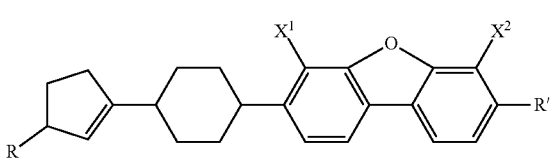

in which $X^1$ and $X^2$ are H or F, R is alkyl and R' is alkyl or alkoxy. However, no specific example of this substance class is described.

One problem addressed by the present invention is that of providing compounds having advantageous properties for use in liquid-crystalline media. They should preferably have negative dielectric anisotropy, which makes them particularly suitable for use in liquid-crystalline media for VA or FFS displays. Irrespective of the dielectric anisotropy corresponding to the display type, what are desired are compounds having a favourable combination of the application-related parameters. Among these parameters that have to be optimized simultaneously, particular mention should be made of a high clearing point, low rotational viscosity and suitable optical anisotropy within the application interval, and of the properties that serve to achieve mixtures having the desired liquid-crystalline phases over a wide temperature range (low melting point, good miscibility with other liquid-crystalline components of the desired type and good solubility coupled with high polarity).

The invention relates to compounds of the formula I

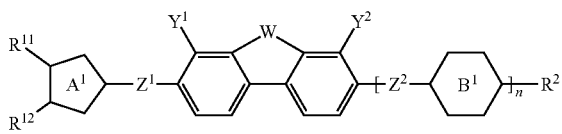

in which
W is —O— or —S—,
$Y^1$ and $Y^2$ are independently H, F, Cl, CN or $CF_3$,
$R^{11}$ and $R^{12}$ are independently H, an unsubstituted, mono-CN— or —$CF_3$-substituted or at least mono-halogen-substituted alkyl- or alkenyl radical having up to 15 carbon atoms, where one or more $CH_2$ groups in these radicals may also be replaced by —O—, —S—, —C≡C—, —$CF_2$O—, —O$CF_2$—, —OC—O— or —O—CO— such that oxygen atoms are not bonded directly to one another,
$R^2$ is an unsubstituted, mono-CN— or —$CF_3$-substituted or at least mono-halogen-substituted alkyl- or alkenyl radical having up to 15 carbon atoms, where one or more $CH_2$ groups in these radicals may also be replaced by —O—, —S—, —C≡C—, —$CF_2$O—, —O$CF_2$—, —OC—O— or —O—CO— such that oxygen atoms are not bonded directly to one another, and also H, halogen, CN, SCN or $SF_5$.
$A^1$ is a 1,3-cyclopentylene radical which may be mono-unsaturated and which may be mono- or polysubstituted by an L group,
$B^1$ is the same or different at each instance and is
  a) a 1,4-phenylene radical in which one or two CH groups may be replaced by N,
  b) a 1,4-cyclohexenylene or 1,4-cyclohexylene radical in which one or two nonadjacent $CH_2$ groups may be replaced by —O— or —S—, a cyclobutane-1,3-diyl radical,
  c) a radical from the group of 1,4-bicyclo[2,2,2]-octylene, spiro[3.3]heptane-2,6-diyl, naphthalene-2,6-diyl, decahydronaphthalene-2,6-diyl, 1,2,3,4-tetrahydronaphthalene-2,6-diyl, thiophene-2,5-diyl, where the groups a), b) and c) may be mono- or polysubstituted by an L group,
L at each instance is independently F, Cl, CN, SCN, $SF_5$ or straight-chain or branched, in each case optionally fluorinated alkyl, alkoxy, alkylcarbonyl, alkoxycarbonyl, alkylcarbonyloxy or alkoxycarbonyloxy having 1 to 12 carbon atoms,
$Z^1$ and $Z^2$ are each independently a single bond, —$CF_2$O—, —O$CF_2$—, —$CF_2$S—, —$SCF_2$—, —$CH_2CH_2$—, —$CF_2CF_2$—, —$CF_2CH_2$—, —$CH_2CF_2$—, —CHF—CHF—, —C(O)O—, —OC(O)—, —$CH_2$O—, —O$CH_2$—, —$CH_2$S—, —$SCH_2$—, —CF=CH—, —CH=CF—, —CF=CF—, —CH=CH— or —C≡C—,
n is 0, 1 or 2.

The compounds have a markedly negative dielectric anisotropy (Δε) and are therefore particularly suitable for use in liquid-crystal mixtures for VA-TFT displays or displays of the IPS or FFS type. A Δε of maximum negativity may be advantageous for applications. The compounds of the invention have a dielectric anisotropy Δε of preferably −4 or less, preferably of −6 or less and most preferably of −8 or less. They exhibit good miscibility with the customary substances used in liquid-crystal mixtures for displays, meaning that they have good solubility therein. The rotational viscosities of the compounds and the resulting liquid-crystalline mixtures are advantageously small, and the respective clearing points at the same time are advantageously high.

The further physical, physicochemical and electrooptical parameters of the compounds of the invention are also advantageous for the use of the compounds in liquid-crystalline media. The liquid-crystalline media comprising these compounds especially have a sufficient breadth of the nematic phase and good low-temperature and long-term stability, and also sufficiently high clearing points. The low melting points of the compounds of the invention suggest the advantageous mixing characteristics. In addition, the inventive compounds of the formula 1, especially for use in VA-TFT displays or displays of the IPS or FFS type, have suitable values for optical anisotropy Δn. Preferably, the compounds of the invention have a Δn of greater than 0.15 and less than 0.25. Moreover, the compounds are relatively easy to prepare. The balanced combination of these advantageous properties constitutes a significant addition to the mixture components available for mixtures having negative dielectric anisotropy.

If $R^{11}$, $R^{12}$ and $R^2$ in formula I are each independently an alkyl radical, these are straight-chain or branched. Preferably, each of these radicals is a straight-chain and, unless stated otherwise, has 1, 2, 3, 4, 5, 6 or 7 carbon atoms and is accordingly preferably methyl, ethyl, propyl, butyl, pentyl, hexyl or heptyl.

If $R^{11}$, $R^{12}$ and $R^2$ in formula I are each independently an alkoxy radical, these are straight-chain or branched. Preferably, each of these radicals is a straight-chain and, unless stated otherwise, has 1, 2, 3, 4, 5, 6 or 7 carbon atoms and is accordingly preferably methoxy, ethoxy, propoxy, butoxy, pentoxy, hexoxy or heptoxy.

$R^{11}$, $R^{12}$ and $R^2$ in formula I may also each independently be an alkenyl radical having 2 to 15 carbon atoms which is straight-chain or branched and has at least one C—C double bond. It is preferably straight-chain and has 2 to 7 carbon atoms. It is accordingly preferably vinyl, prop-1- or prop-2-enyl, but-1-, 2- or but-3-enyl, pent-1-, 2-, 3- or pent-4-enyl, hex-1-, 2-, 3-, 4- or hex-5-enyl, hept-1-, 2-, 3-, 4-, 5- or hept-6-enyl. If the two carbon atoms of the C—C double bond are substituted, the alkenyl radical may be in the form of the E and/or Z isomer (trans/cis). In general, preference is given to the respective E isomers. Among the alkenyl radicals, particular preference is given to prop-2-enyl, 2- or but-3-enyl, and 3- or pent-4-enyl.

$R^{11}$, $R^{12}$ and $R^2$ in formula I may independently also be an alkynyl radical having 2 to 15 carbon atoms which is straight-chain or branched and has at least one C—C triple bond. Preference is given to 1- or 2-propynyl and 1-, 2- or 3-butynyl.

If $R^2$ is a polar radical, it is selected from halogen, CN, SCN, $SF_5$, mono-, di- or polyfluorinated alkyl, alkenyl, alkoxy or alkenyloxy having up to 15 carbon atoms, preferably F, Cl, CN, SCN, SF$_5$, CF$_2$H, CF$_3$, OCF$_2$H, OCF$_3$ or —OCH=CF$_2$.

The Z$^1$ group is preferably a single bond, —CH$_2$O—, —OCH$_2$—, —CF$_2$O— or —OCF$_2$, more preferably a single bond.

The Z$^2$ group is preferably a single bond, —CH$_2$O—, —OCH$_2$—, —CF$_2$O— or —OCF$_2$, more preferably a single bond.

Preferably, the ring element B$^1$ is selected from the group of ring elements of the formulae

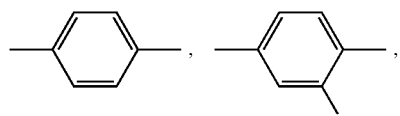,
,
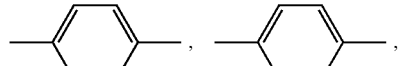,
,
,
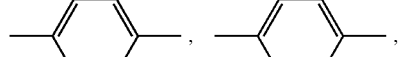,
,
,
,
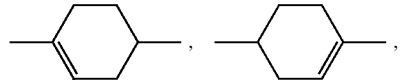,
,
,
,
,
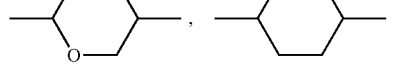,
 and more preferably

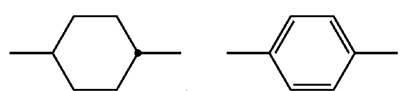,
,
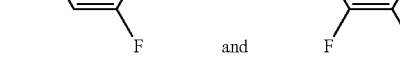

most preferably

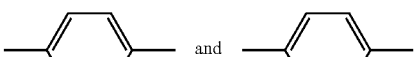 and 

Preferably, A$^1$ is selected from the ring elements of the formulae

,
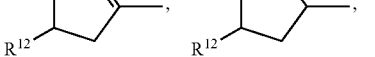,
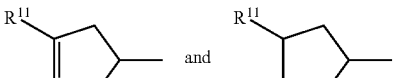

more preferably

,
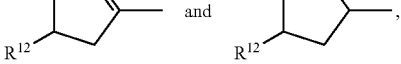

most preferably

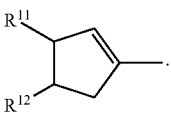.

In these formulae, R$^{11}$ and R$^{12}$ are independently preferably H or alkyl having 1 to 7 carbon atoms.

More preferably, at least one of the R$^{11}$ and R$^{12}$ groups is H.

In a very particularly preferred embodiment, R$^{11}$ and R$^{12}$ are both H.

In a preferred embodiment of the present invention, W is —S—.

Halogen in the context of the present invention is fluorine, chlorine, bromine and iodine, especially fluorine and chlorine.

The L group is preferably F, Cl, —CF$_3$ or an alkyl or alkoxy group having 1, 2 or 3 carbon atoms.

Preferably, at least one of the Y$^1$ and Y$^2$ radicals in formula I is not H.

More preferably, Y$^1$ and Y$^2$ in formula I are both F.

Preferably, n is 0 or 1, more preferably 0.

The compounds of the formula I are preferably selected from the group of compounds of the formulae I-1 and I-2.

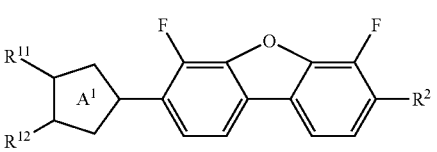

I-1

I-2

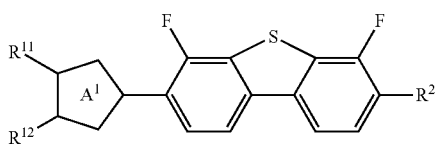

in which $R^{11}$, $R^{12}$ and $R^2$ have the definitions given above.

Very particular preference is given to the compounds of the formula I-2.

The compounds of the formulae I-1 and I-2 are preferably selected from the group of compounds of the following subformula:

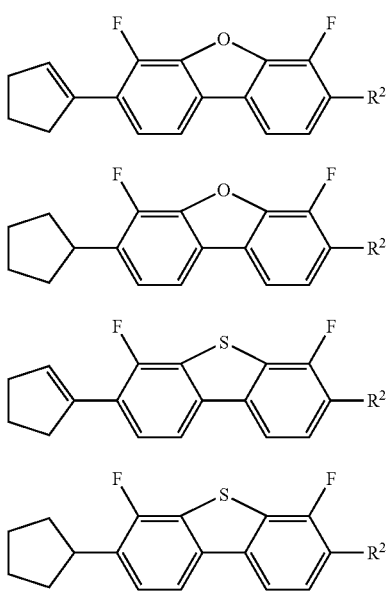

I-1a

I-1b

I-2a

I-2b in which $R^2$ has the definition given above.

In a first preferred embodiment, $R^2$ in the formulae I-1a, I-1b, I-2a and I-2b is methyl, ethyl, n-propyl, n-butyl, n-pentyl, n-hexyl or n-heptyl.

In a second preferred embodiment, $R^2$ in the formulae I-1a, I-1 b, I-2a and I-2b is methoxy, ethoxy, n-propoxy, n-butoxy, n-pentoxy, n-hexoxy or n-heptoxy.

In a third preferred embodiment, $R^2$ in the formulae I-1a, I-1b, I-2a and I-2b is F, Cl, CN, SCN, $SF_5$, $CF_2H$, $CF_3$, $OCF_2H$, $OCF_3$ or —OCH=$CF_2$, more preferably F, $CF_3$ or $OCF_3$.

If radicals or substituents in the compounds of the invention or the compounds of the invention themselves are in the form of optically active or stereoisomeric radicals, substituents or compounds because they have an asymmetric centre, for example, these are also encompassed by the present invention. It is obvious here that the inventive compounds of the general formula I may be in isomerically pure form, for example in the form of pure enantiomers, diastereomers, E or Z isomers, trans or cis isomers, or in the form of a mixture of multiple isomers in any ratio, for example of a racemate, E/Z isomer mixture or cis/trans isomer mixture.

The 1,4-substituted cyclohexyl ring of the formula

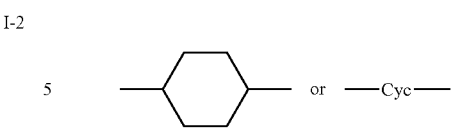

in the disclosed compounds for liquid-crystalline media preferably has trans configuration, meaning that the two substituents, in the thermodynamically preferred chair conformation, are both in equatorial position.

The compounds of the general formula I can be prepared by methods known per se, as described in the literature (for example in the standard works such as Houben-Weyl, Methoden der organischen Chemie [Methods of Organic Chemistry], Georg-Thieme-Verlag, Stuttgart), under the reaction conditions which are known and suitable for the reactions mentioned. It is possible here to make use of variants that are known per se but are not mentioned in detail here.

The starting materials may optionally also be formed in situ, in such a way that they are not isolated from the reaction mixture but are immediately converted further to the compounds of the general formula I.

The syntheses of inventive compounds of the general formula I are described by way of example in the examples. The starting substances are obtainable by commonly accessible literature methods or commercially.

A particularly preferred synthesis route is shown in Scheme 1:

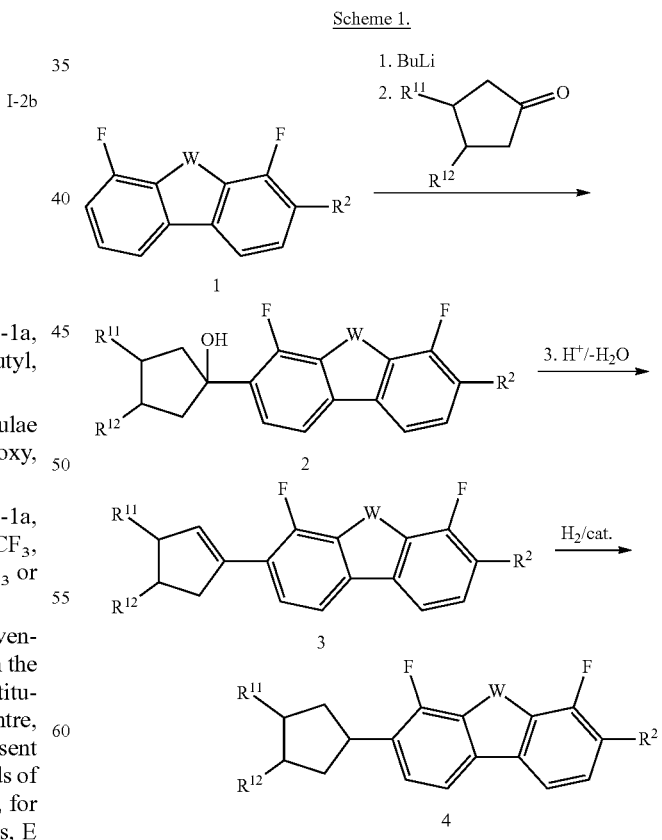

Suitable precursors (1) are described in WO 02/055463 and DE 10 2015 002298 A1 (for W=O, $R^2$=alkyl, alkoxy), in EP 2 937 342 A1 (for W=S, R²=alkyl, alkoxy) and in EP 3 085 753 A1 (for W=O, S, R²=F, Cl, CN, SCN, SF₅, CF₂H, CF₃, OCF₂H, OCF₃ or —OCH=CF₂). The compounds 1, after ortho-metallation, addition to correspondingly substituted cyclopentanone derivatives to give the alcohols 2 and subsequent elimination of water, afford the inventive products 3 which may, if appropriate, be converted further by catalytic hydrogenation to the inventive compounds 4. Preferred conditions for the metallation are reaction with a lithium alkyl such as n-BuLi, in THF, at about −70° C., then addition of the ketone.

Cyclopentanone and alkyl- and dialkylcyclopentanone derivatives are commercially available and known from the literature, or can be prepared in a manner analogous to the syntheses known from the literature, either as a racemate or in optically active form. Preference is given in accordance with the present invention to using alkyl-substituted cyclopentanones as racemates.

Examples of preferred cyclopentanone derivatives are:

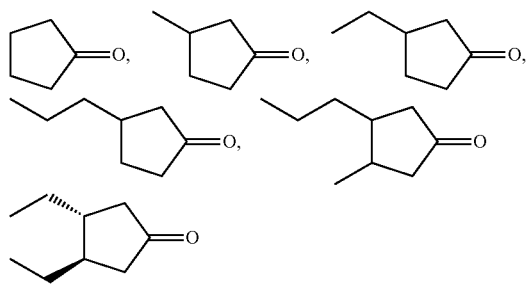

The invention further provides compounds of the formula II

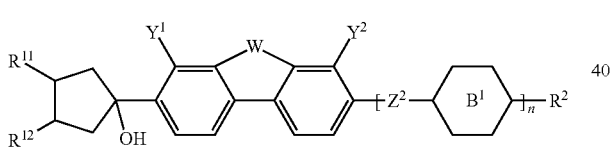

in which $R^{11}$, $R^{12}$, $Y^1$, $Y^2$, W, $Z^2$, $B^1$, $R^2$ and n have the definitions given for formula I.

Compounds of the formula II are prepared by the syntheses specified in Scheme 1 and in the working examples and can be converted to the compounds of the formula I by elimination of water.

Methods for elimination of water from alcohols are known to those skilled in the art and are described, for example, in Houben-Weyl, Methoden der organischen Chemie, Georg-Thieme-Verlag, Stuttgart.

The process and the subsequent workup of the reaction mixture can in principle be conducted as a batchwise reaction or in continuous reaction mode. The continuous reaction mode comprises, for example, reaction in a continuous stirred tank reactor, a stirred tank cascade, a loop or cross-flow reactor, a flow tube or a microreactor. The reaction mixtures are worked up as required by any of the following methods: by filtration through solid phases, chromatography, separation between immiscible phases (e.g. extraction), adsorption on solid supports, distillative removal of solvents and/or azeotropic mixtures, selective distillation, sublimation, crystallization, co-crystallization or nanofiltration on membranes.

As already mentioned, the compounds of the general formula I can be used in liquid-crystalline media. The present invention therefore also provides a liquid-crystalline medium comprising at least two liquid-crystalline compounds, containing at least one compound of the general formula I.

The present invention also provides liquid-crystalline media comprising, as well as one or more inventive compounds of formula I, as further constituents, 2 to 40 and preferably 4 to 30 components. More preferably, these media comprise, as well as one or more compounds of the invention, 7 to 25 components. These further constituents are preferably selected from the group of nematic or nematogenic (monotropic or isotropic) substances, especially substances from the classes of the azoxybenzenes, benzylideneanilines, biphenyls, terphenyls, 1,3-dioxanes, 2,5-tetrahydropyrans, phenyl or cyclohexyl benzoates, phenyl or cyclohexyl cyclohexanecarboxylates, phenyl or cyclohexyl esters of cyclohexylbenzoic acid, phenyl or cyclohexyl esters of cyclohexylcyclohexanecarboxylic acid, cyclohexylphenyl esters of benzoic acid, of cyclohexanecarboxylic acid or of cyclohexylcyclohexanecarboxylic acid, phenylcyclohexanes, cyclohexylbiphenyls, phenylcyclohexylcyclohexanes, cyclohexylcyclohexanes, cyclohexylcyclohexylcyclohexenes, 1,4-biscyclohexylbenzenes, 4',4'-biscyclohexylbiphenyls, phenyl- or cyclohexylpyrimidines, phenyl- or cyclohexylpyridines, phenyl- or cyclohexyldioxanes, phenyl- or cyclohexyl-1,3-dithianes, 1,2-diphenylethanes, 1,2-dicyclohexylethanes, 1-phenyl-2-cyclohexylethanes, 1-cyclohexyl-2-(4-phenylcyclohexypethanes, 1-cyclohexyl-2-biphenylethanes, 1-phenyl-2-cyclohexylphenylethanes, optionally halogenated stilbenes, benzyl phenyl ethers, tolanes and substituted cinnamic acids. The 1,4-phenylene groups in these compounds may also be mono- or polyfluorinated.

The most important compounds that are useful as further constituents of inventive media can be characterized by the formulae (II), (III), (IV), (V) and (VI):

R'-L-E-R"     (II)

R'-L-COO-E-R"     (III)

R'-L-OOC-E-R"     (IV)

R'-L-CH₂CH₂-E-R"     (V)

R'-L-CF₂O-E-R"     (VI)

In the formulae (II), (III), (IV), (V) and (VI), L and E, which may be the same or different, are each independently a bivalent radical from the group formed from -Phe-, -Cyc-, -Phe-Phe-, -Phe-Cyc-, -Cyc-Cyc-, -Pyr-, -Dio-, -Thp-, -G-Phe- and -G-Cyc- and mirror images thereof, where Phe is unsubstituted or fluorine-substituted 1,4-phenylene, Cyc is trans-1,4-cyclohexylene or 1,4-cyclohexenylene, Pyr is pyrimidine-2,5-diyl or pyridine-2,5-diyl, Dio is 1,3-dioxane-2,5-diyl, Thp is tetrahydropyran-2,5-diyl and G is 2-(trans-1,4-cyclohexyl)ethyl, pyrimidine-2,5-diyl, pyridine-2,5-diyl, 1,3-dioxane-2,5-diyl or tetrahydropyran-2,5-diyl.

Preferably, one of the L and E radicals is Cyc or Phe. E is preferably Cyc, Phe or Phe-Cyc. Preferably, the media of the invention comprise one or more components selected from the compounds of the formulae (II), (III), (IV), (V) and (VI) in which L and E are selected from the group of Cyc and Phe and, at the same time, one or more components selected from the compounds of the formulae (II), (III), (IV), (V) and (VI) in which one of the L and E radicals is selected from the group of Cyc and Phe and the other radical is selected from the group of -Phe-Phe-, -Phe-Cyc-, -Cyc-Cyc-, -G-Phe- and -G-Cyc-, and optionally one or more components selected from the compounds of the formulae (II), (III), (IV), (V) and (VI) in which the L and E radicals are selected from the group of -Phe-Cyc-, -Cyc-Cyc-, -G-Phe- and -G-Cyc-.

R' and R" in a smaller subgroup of the compounds of the formulae (II), (III), (IV), (V) and (VI) are each independently alkyl, alkenyl, alkoxy, alkoxyalkyl (oxaalkyl), alkenyloxy or alkanoyloxy having up to 8 carbon atoms. This smaller subgroup is called group A hereinafter, and the compounds are referred to by the subformulae (IIa), (IIIa), (IVa), (Va) and (VIa). In most of these compounds, R' and R" are different from one another, where one of these radicals is usually alkyl, alkenyl, alkoxy or alkoxyalkyl (oxaalkyl).

In another smaller subgroup of the compounds of the formulae (II), (III), (IV), (V) and (VI), referred to as group B, E is

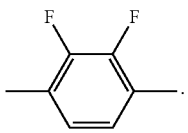

In the compounds of group B that are referred to by the subformulae (IIb), (IIIb), (IVb), (Vb) and (VIb), R' and R" have the definition given for the compounds of the subformulae (IIa) to (VIa) and are preferably alkyl, alkenyl, alkoxy or alkoxyalkyl (oxaalkyl).

In a further smaller subgroup of the compounds of the formulae (II), (III), (IV), (V) and (VI), R" is —CN. This subgroup is referred to hereinafter as group C, and the compounds of this subgroup are correspondingly described by subformulae (IIc), (IIIc), (IVc), (Vc) and (VIc). In the compounds of the subformulae (IIb), (IIIb), (IVb), (Vb) and (VIb), R' has the definition given for the compounds of the subformulae (IIa) to (VIa) and is preferably alkyl, alkenyl, alkoxy or alkoxyalkyl (oxaalkyl).

As well as the preferred variants of groups A, B and C, other compounds of the formulae (II), (III), (IV), (V) and (VI) with other variants of the substituents envisaged are also in common use. All these substances are obtainable by methods known from the literature or in analogy thereto.

The media of the invention comprise, as well as the inventive compounds of the general formula I, preferably one or more compounds from groups A, B and/or C. The proportions by mass of the compounds from these groups in the media of the invention are:

Group A:
0% to 90%, preferably 20% to 90%, especially 30% to 90%.

Group B:
0% to 80%, preferably 10% to 80%, especially 10% to 70%.

Group C:
0% to 80%, preferably 5% to 80%, especially 5% to 50%.

The media of the invention contain preferably 1% to 40%, more preferably 5% to 30%, of the inventive compounds of the formula I. The media comprise preferably one, two, three, four or five inventive compounds of the formula I.

The media of the invention are produced in a customary manner per se. In general, the components are dissolved in one another, preferably at elevated temperature. By means of suitable additions, the liquid-crystalline phases of the present invention can be modified such that they can be used in all types of liquid-crystal display elements that have become known to date. Additions of this kind are known to those skilled in the art and described in detail in the literature (H. Kelker/R. Hatz, Handbook of Liquid Crystals, Verlag Chemie, Weinheim, 1980). For example, pleochroic dyes can be added for production of coloured guest-host systems, or substances for altering the dielectric anisotropy, the viscosity and/or the orientation of the nematic phases.

Owing to their negative $\Delta\varepsilon$, the compounds of the formula I are especially suitable for use in VA-TFT displays.

The present invention therefore also provides electrooptical display elements comprising a liquid-crystalline medium of the invention. Preferably, the display element is a VA-TFT display element (VA: vertical alignment, TFT: thin-film transistor).

Further combinations of the embodiments and variants of the invention according to the description are apparent from the claims.

Further embodiments of the present invention are apparent from the claims and from combinations of two or more of these claims.

The invention is elucidated in detail hereinafter by working examples, but without any intention to restrict it thereto. The person skilled in the art will be able to infer details of procedure from the examples that are not specifically listed in the general description, generalize them according to common art knowledge and apply them to the specific problem of interest.

As well as the customary and well-known abbreviations, the following abbreviations are used:

K: crystalline phase; N: nematic phase; Sm: smectic phase;

I: isotropic phase. The numbers between these symbols indicate the transition temperatures of the substance in question.

Unless stated otherwise, temperature figures are in ° C.

The determination of physical, physicochemical and electrooptical parameters is effected by commonly known methods as described inter alia in the brochure "Merck Liquid Crystals—Licristal®—Physical Properties of Liquid Crystals—Description of the Measurements Methods", 1998, Merck KGaA, Darmstadt.

Above and hereinafter, $\Delta n$ denotes optical anisotropy (589 nm, 20° C.) and $\Delta\varepsilon$ dielectric anisotropy (1 kHz, 20° C.). Dielectric anisotropy $\Delta\varepsilon$ is determined at 20° C. and 1 kHz. Optical anisotropy $\Delta n$ is determined at 20° C. and a wavelength of 589.3 nm.

The $\Delta\varepsilon$ and $\Delta n$ values, the extrapolated clearing point (Clp.) and the rotational viscosity ($\gamma_1$) of the compounds of the invention are obtained by linear extrapolation from liquid-crystalline mixtures consisting to an extent of 5% to 10% of the respective compound of the invention and to an extent of 90-95% of the commercially available liquid-crystal mixture ZLI-2857 (for $\Delta\varepsilon$, Clp.) or ZLI-4792 (for $\Delta n$, $\gamma_1$) (mixtures from Merck KGaA, Darmstadt).

The abbreviations hereinafter mean:
RT room temperature, about 20° C.
m.p. melting point
MTB methyl tert-butyl ether
THF tetrahydrofuran
EA ethyl acetate
BuCl n-butyl chloride
TsOH toluenesulfonic acid
BuLi n-butyllithium The synthesis of compound 1 is described in DE 10 2015 004271 A1.

SUBSTANCE EXAMPLE 1

1.1 1-(7-Ethoxy-4,6-difluorodibenzothiophen-3-yl)cyclopentanol (3)

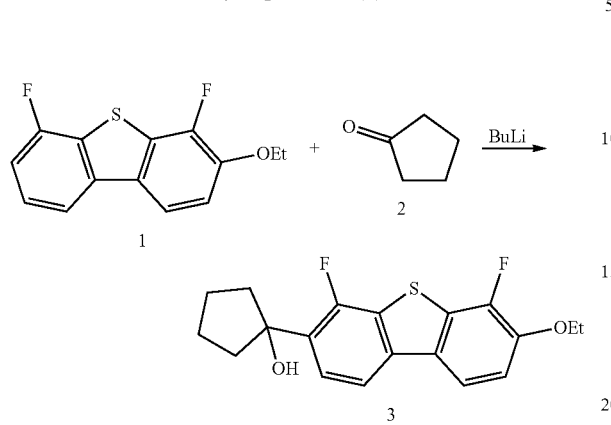

5.3 g (20 mmol) of the dibenzothiophene 1 are dissolved in 50 ml of THF and, at −70° C., 16.9 ml of butyllithium (15%) in hexane (26 mmol) are added. After 1 h at −70° C., 2.3 g (30 mmol) of cyclopentanone (2), dissolved in 20 ml of THF, are added. The cooling is removed and, at −20° C., water and MTB ether are added to the mixture. The aqueous phase is extracted with MTB ether, and the combined organic phases are dried over sodium sulfate, filtered and concentrated. The residue is filtered through silica gel (BuCl/EA) and the product fractions are concentrated. The residue obtained (2.5 g (81%)) (3) is used in the subsequent stage without further purification.

1.2 3-(Cyclopenten-1-yl)-7-ethoxy-4,6-difluorodibenzothiophene (4)

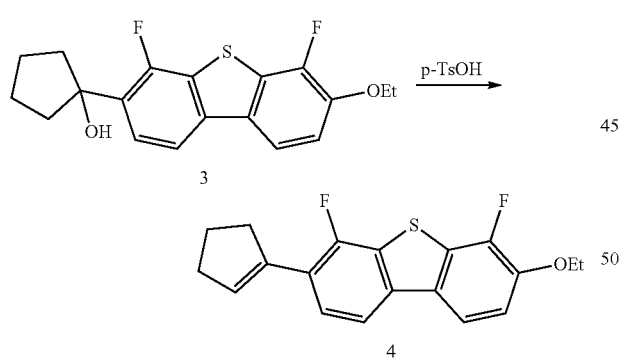

3.5 g (10 mmol) of alcohol 3 are dissolved in 80 ml of toluene, 200 mg of p-TsOH are added and the mixture is heated to boiling on a water trap. The cooled mixture is filtered through silica gel and eluted with n-heptane. The residue obtained after concentration of the filtrate is crystallized from ethanol/toluene. This affords 3-(cyclopenten-1-yl)-7-ethoxy-4,6-difluorodibenzothiophene as colourless crystals of m.p. 153° C.

$\Delta\varepsilon = -8.24$ $\Delta n = 0.2815$ $\gamma_1 = 235$ m Pa s

Example 2: 3-(Cyclopentyl)-7-ethoxy-4,6-difluorodibenzothiophene (4)

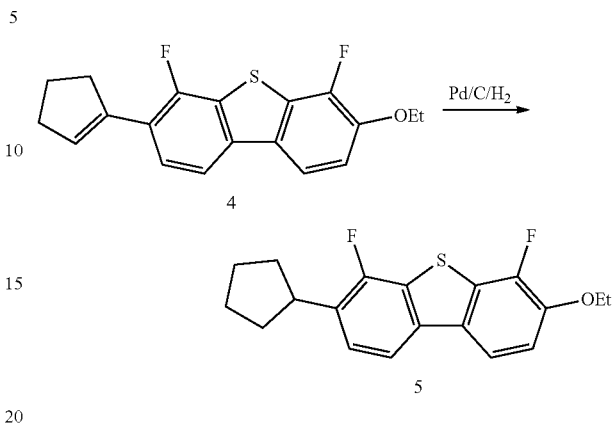

5.3 g (20 mmol) of the cyclopentene 4 are dissolved in 55 ml of THF and hydrogenated to completion over Pd/C. The solution is then filtered and concentrated, and the residue is filtered through silica gel with n-heptane/EA and recrystallized from ethanol and then from heptane. This affords 3-(cyclopentyl)-7-ethoxy-4,6-difluorodibenzothiophene as colourless crystals of m.p. 110° C.

$\Delta\varepsilon = -8.41$ $\Delta n = 0.2035$ $\gamma_1 = 276$ m Pa s

The invention claimed is:

1. Compound of the formula I

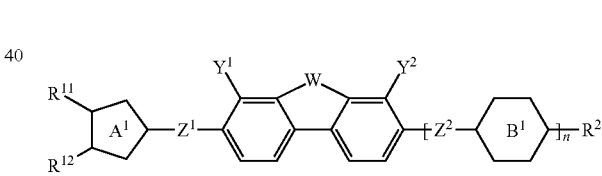

in which

W is —S—, $Y^1$ and $Y^2$ are independently H, F, Cl, CN or $CF_3$, $R^{11}$ and $R^{12}$ are independently H, an unsubstituted, mono-CN— or —$CF_3$-substituted or at least mono-halogen-substituted 1 to 15 carbon atom alkyl radical or 2 to 15 carbon atom alkenyl radical, where one or more $CH_2$ groups in these radicals may also be replaced by —O—, —S—, —C≡C—, —$CF_2$O—, —$OCF_2$—, —OC—O— or —O—CO— such that oxygen atoms are not bonded directly to one another, $R^2$ is an unsubstituted, mono-CN— or —$CF_3$-substituted or at least mono-halogen-substituted 1 to 15 carbon atom alkyl radial or 2 to 15 carbon atom alkenyl radical, where one or more $CH_2$ groups in these radicals may also be replaced by —O—, —S—, —C≡C—, —$CF_2$O—, —$OCF_2$—, —OC— O— or —O—CO— such that oxygen atoms are not bonded directly to one another, and also H, halogen, CN, SCN or $SF_5$, $A^1$ with the $R^{11}$ and $R^{12}$ groups, is

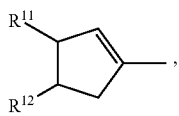

$B^1$ is the same or different at each instance and is
  a) a 1,4-phenylene radical in which one or two CH groups may be replaced by N,
  b) a 1,4-cyclohexenylene or 1,4-cyclohexylene radical in which one or two nonadjacent $CH_2$ groups may be replaced by —O— or —S—, a cyclobutane-1,3-diyl radical,
  c) a radical from the group of 1,4-bicyclo[2,2,2]-octylene, spiro[3.3]heptane-2,6-diyl, naphthalene-2,6-diyl, decahydronaphthalene-2,6-diyl, 1,2,3,4-tetrahydronaphthalene-2,6-diyl, or thiophene-2,5-diyl,
  where the groups a), b) and c) may be mono- or polysubstituted by an L group,
L at each instance is independently F, Cl, CN, SCN, $SF_5$ or straight-chain or branched, in each case optionally fluorinated alkyl, alkoxy, alkylcarbonyl, alkoxycarbonyl, alkylcarbonyloxy or alkoxycarbonyloxy having 1 to 12 carbon atoms or 3 to 12 carbon atoms if branched,
$Z^1$ and $Z^2$ are each independently a single bond, —$CF_2O$—, —$OCF_2$—, —$CF_2S$—, —$SCF_2$—, —$CH_2CH_2$—, —$CF_2CF_2$—, —$CF_2CH_2$—, —$CH_2CF_2$—, —CHF—CHF—, —C(O)O—, —OC(O)—, —$CH_2O$—, —$OCH_2$—, —$CH_2S$—, —$SCH_2$—, —CF=CH—, —CH=CF—, —CF=CF—, —CH=CH— or —C≡C—,
n is 0, 1 or 2.

2. Compound of the formula I according to claim 1, characterized in that B is selected from the group of ring elements of the formulae

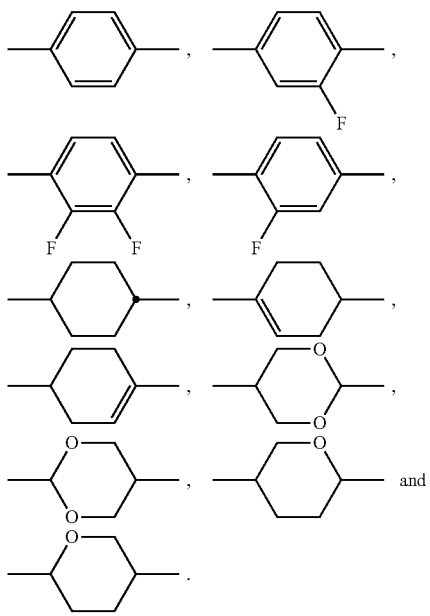

3. Compound of the formula I according to claim 1, characterized in that at least one of the $Y^1$ and $Y^2$ radicals is not H.

4. Compound of the formula I according to claim 1, characterized in that $Y^1$ and $Y^2$ are both F.

5. Compound according to claim 1, characterized in that $R^2$ is methyl, ethyl, n-propyl, n-butyl, n-pentyl, n-hexyl or n-heptyl.

6. Compound according to claim 1, characterized in that $R^2$ is methoxy, ethoxy, n-propoxy, n-butoxy, n-pentoxy, n-hexoxy or n-heptoxy.

7. Compound according to claim 1, characterized in that $R^2$ is F, Cl, CN, SCN, $SF_5$, $CF_2H$, $CF_3$, $OCF_2H$, $OCF_3$ or —OCH=$CF_2$.

8. Compound of the formula II

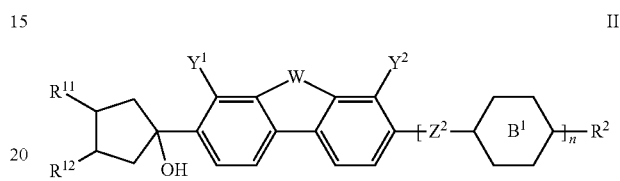

in which
$R^{11}$ and $R^{12}$ are independently H, an unsubstituted, mono-CN— or —$CF_3$-substituted or at least mono-halogen-substituted 1 to 15 carbon atom alkyl radical or 2 to 15 carbon atom alkenyl radical, where one or more $CH_2$ groups in these radicals may also be replaced by —O—, —S—, —C≡C—, —$CF_2O$—, —$OCF_2$—, —OC—O— or —O—CO— such that oxygen atoms are not bonded directly to one another,
$Y^1$ and $Y^2$ are independently H, F, Cl, CN or $CF_3$,
W is —O— or —S—,
$Z^2$ are each independently a single bond, —$CF_2O$—, —$OCF_2$—, —$CF_2S$—, —$SCF_2$—, —$CH_2CH_2$—, —$CF_2CF_2$—, —$CF_2CH_2$—, —$CH_2CF_2$—, —CHF—CHF—, —C(O)O—, —OC(O)—, —$CH_2O$—, —$OCH_2$—, —$CH_2S$—, —$SCH_2$—, —CF=CH—, —CH=CF—, —CF=CF—, —CH=CH— or —C≡C—,
$B^1$ is the same or different at each instance and is
  a) a 1,4-phenylene radical in which one or two CH groups may be replaced by N,
$R^2$ is an unsubstituted, mono-CN— or —$CF_3$-substituted or at least mono-halogen-substituted 1 to 15 carbon atom alkyl radical or 2 to 15 carbon atom alkenyl radical, where one or more $CH_2$ groups in these radicals may also be replaced by —O—, —S—, —C≡C—, —$CF_2O$—, —$OCF_2$—, —OC—O— or —O—CO— such that oxygen atoms are not bonded directly to one another, and also H, halogen, CN, SCN or $SF_5$,
n is 0, 1 or 2.

9. Liquid-crystalline medium, which comprises one or more compounds according to claim 1.

10. Electrooptical display element, which comprises a liquid-crystalline medium according to claim 9.

11. Compound of the formula I according to claim 1, wherein the compound is of the formula I-2:

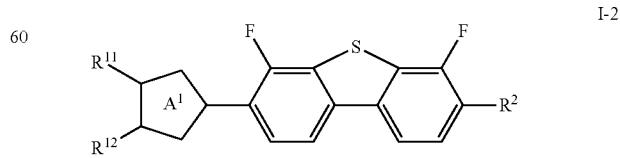

* * * * *